United States Patent [19]

Toda

[11] 4,329,869
[45] May 18, 1982

[54] APPARATUS FOR MEASURING THE AMOUNT OF AIR BUBBLES CONTAINED IN LIQUID

[75] Inventor: Kenichi Toda, Anjyo, Japan

[73] Assignee: Kabushiki Kaisha Polyurethan Engineering, Tokyo, Japan

[21] Appl. No.: 150,099

[22] Filed: May 15, 1980

[30] Foreign Application Priority Data

Jul. 27, 1979 [JP] Japan .................................. 54-96612

[51] Int. Cl.$^3$ .............................................. G01N 7/00
[52] U.S. Cl. ........................................ 73/19; 73/61 R
[58] Field of Search .................................. 73/61 R, 19

[56] References Cited

U.S. PATENT DOCUMENTS 2,138,141 11/1938 Cromer et al. ........................... 73/19
3,968,678 7/1976 Krener et al. ............................ 73/19
4,050,896 9/1977 Raffel et al. ......................... 73/19 X
4,089,206 5/1978 Raffel et al. .............................. 73/19

FOREIGN PATENT DOCUMENTS 974183 11/1964 United Kingdom .................... 73/19

Primary Examiner—Kyle L. Howell
Assistant Examiner—Joseph W. Roskos
Attorney, Agent, or Firm—Armstrong, Nikaido, Marmelstein & Kubovcik

[57] ABSTRACT

A method and apparatus for measuring the amount of air bubbles contained in liquid, in which the liquid is introduced in a closed space and is then twice pressed under different pressures to compress the air bubbles in the liquid in order to provide two liquids having different pressures, and the pressures of the two liquids are measured by a pressure gage to determine the amount of air bubbles. The apparatus comprises a container defining a closed space in which the liquid to be measured is introduced, a cylinder which is connected to the closed space and which has therein a movable piston, and a pressure gage which measures the pressure of the liquid.

2 Claims, 3 Drawing Figures

APPARATUS FOR MEASURING THE AMOUNT OF AIR BUBBLES CONTAINED IN LIQUID

BACKGROUND OF THE INVENTION

This invention relates to a method and an apparatus for measuring the amount of air bubbles contained in incompressible liquid, and particularly to a method and an apparatus for measuring the amount of air bubbles mixed in incompressible liquid, in which the liquid to be measured containing air bubbles is introduced in a closed space and is then twice pressed under different pressures to compress the air bubbles in the liquid in order to provide two optional and different volumes of liquid, and the pressures of the two liquids having different pressures are measured by a pressure gage to determine the amount of air bubbles.

For instance, when a polyurethan resin is molded, air is preliminarily mixed with the liquid material. However, it is very difficult to precisely measure the amount of the mixed air.

Prior to the completion of this invention, the inventor had experimentally tried to measure the amount of the air bubbles contained in liquid to be measured, in such a way that a predetermined pressure was applied to the liquid containing air bubbles and the pressure was then released therefrom to move a piston of a cylinder or the like upward due to the stored energy, i.e. the pressure of the compressed air bubbles and then the displacement of the piston was measured. The inventor found as the result of the experiment that an exact measurement of the amount of air bubbles can not be effected in this way, because a high pressure of the air bubbles, enough to raise the piston, can not be obtained due to the large mechanical resistance of the piston and the cylinder.

SUMMARY OF THE INVENTION

The present invention is, therefore, directed to an improvement of the experimentally tried method and apparatus. According to the present invention, the liquid to be measured containing air bubbles is twice pressed to compress the air bubbles in the liquid so that two optional and different volumes of liquid are provided, and the pressures of two liquids having different volumes are measured to determine the amount of compressed air bubbles contained in the liquid. In this way, it is confirmed that the measurement can be effected without being influenced by the mechanical resistance of the piston and the cylinder or the like.

BRIEF DESCRIPTION OF THE DRAWINGS

The invention will be discussed below in detail with reference to the drawings, in which.

DETAILED DESCRIPTION OF THE INVENTION

Figure 1:
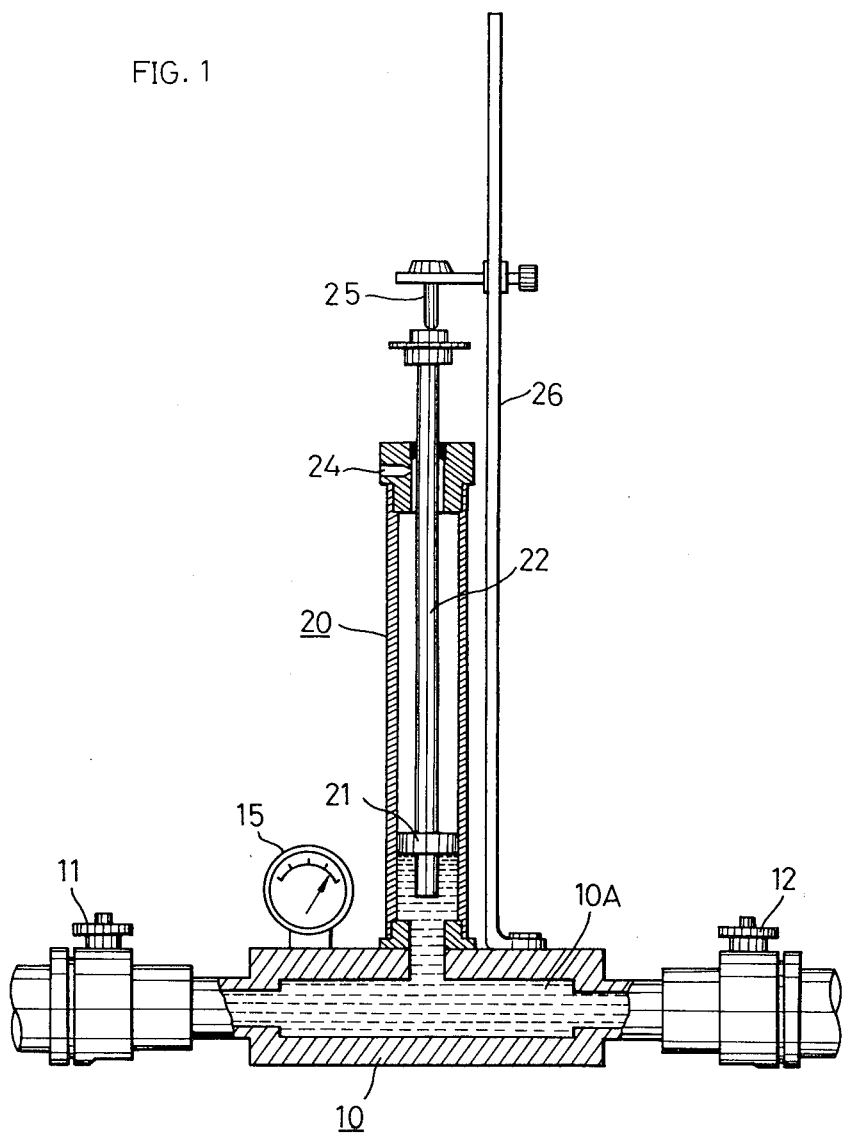
FIG. 1 is a partially sectioned side elevational view of an embodiment of an apparatus for carrying out the method of invention.

In this invention, first, with reference to FIG. 1, the liquid to be measured containing air bubbles is introduced in a closed space 10A of a pipe 10. The closed space 10A in the pipe 10 is defined by two valves 11,12 located in the pipe 10, as illustrated in FIG. 1. The pipe 10 is equipped with a liquid pressure gage 15 which measures the pressure of the liquid within the closed space 10A. The pipe 10 is provided with a cylinder 20 which is connected to said closed space 10A and which has therein a slidable cylinder piston 21 with a piston rod 22. The piston rod 22 can be connected, at its upper end, to a stop 25 which movable in an upwards and downwards direction along a strut 26 extending from the pipe 10. The displacement of the piston rod 22 causes the volume of air bubbles, and accordingly, the volume of the liquid to vary. The stop 25 can be immovably fixed to the strut 26 at any position. When stop 25 is set at a position, the upward displacement of the piston rod 22 is limited by the stop 25. Thus, the displacement of the stop 25 causes air bubbles contained in the liquid in the closed space 10A to be compressed. Therefore, optional and different volumes of liquid can be obtained by adjusting the stop 25. In FIG. 1, the numeral 24 denotes an air bleed hole.

Referring now to the operation of the abovementioned apparatus, a measuring method of this invention will be discussed below.

Figure 2:
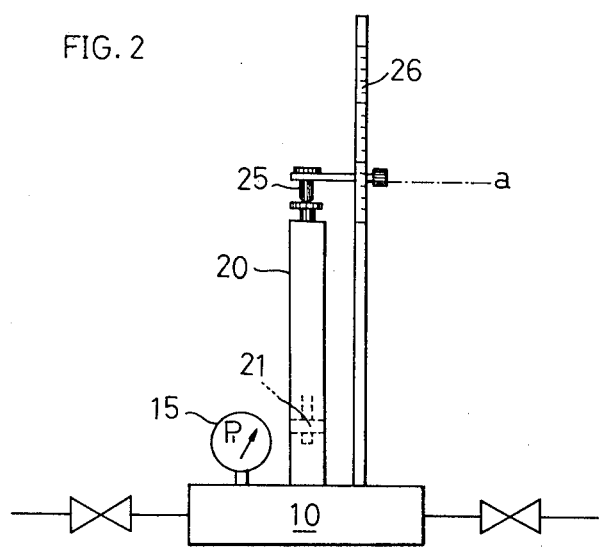
FIG. 2 is a schematic side elevational view of the apparatus of FIG. 1, shown in its first compressed position in which air bubbles in the liquid to be measured are compressed under a first pressure.
Figure 3:
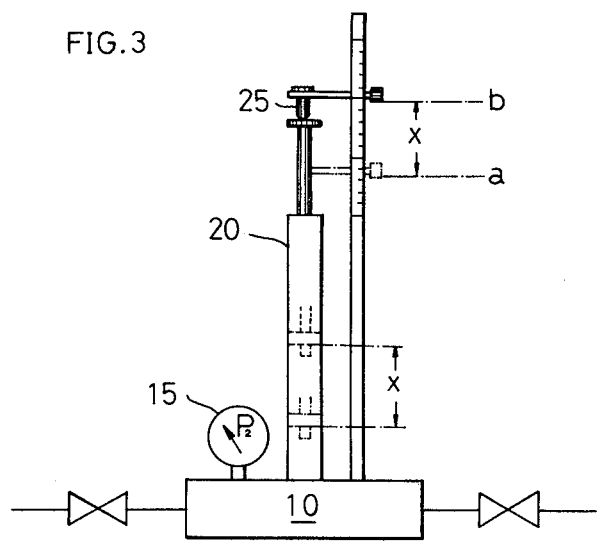
FIG. 3 is a schematic side elevational view of the apparatus of FIG. 1, shown in its second compressed position in which the air bubbles are compressed under a second pressure different from the first pressure.

First, the stop 25 is set at an optional position a (first compressed position) (FIG. 2), and the liquid to be measured is introduced into the closed space 10A under a pressure (first pressure). Then, the first pressure of the enclosed liquid is measured by the liquid pressure gage 15 (see FIG. 2). The first liquid pressure thus measured is P1 Kg/cm² (absolute pressure). After that, the stop 25 is moved to another optional position b (second compressed position) different from the first compressed position a, and the second liquid pressure at this position b is measured by the gage 15 (FIG. 3). The second liquid pressure thus obtained is a pressure at expantion and is designated by P2 Kg/cm² (absolute pressure) which is smaller than P1.

When the displacement distance (b-a) of the stop 25 (i.e. an elevation distance of the piston 21) is Lcm, the volume of the closed space is V cm³, the sectional area of the cylinder is D cm², and the air bubbles' volume is A cm³ (1 atm. wherein 1 atm=1.033 Kg/cm²), then the following equation is obtained according to Boyle's law.

$$\frac{1.033\,A}{P2} - \frac{1.033\,A}{P1} = L\,D \qquad (1)$$
$$\therefore A = \frac{P1\,P2\,L\,D}{1.033(P1 - P2)}$$

On the other hand, the volume V L of pure liquid material which does not contain any air bubbles can be obtained from the following equation.

$$VL = V - \frac{1.033\,A}{P1}$$

By substituting this equation by the equation (1), the following equation (2) is obtained.

$$VL = V - \frac{P2\,L\,D}{P1 - P2} \qquad (2)$$

Consequently, the amount Y(%) of the air bubbles contained in the liquid is as follows.

$$Y = \frac{A}{VL + A} \times 100$$

Therefore, by substituting this equation by the equation (1) and (2), the following equation is obtained.

$$Y = \frac{P1P2\,LD}{1.033\,\{V(P1 - P2) - P2LD\} + P1P2LD} \times 100 \qquad (3)$$

Wherein Y is a volume % under 1 atm. Thus, the amount (volume % under 1 atm.) of air bubbles contained in the liquid can be calculated by substituting the equation (3) by the measurement of P1 and P2.

As can be understood from the above discussion, according to the invention, only the measurement of pressures of liquids having two optional and different volumes (i.e. the pressure of compressed air bubbles) is required to determine the amount of the air bubbles contained in the liquid. Furthermore, since the displacement distance of the piston 21 is limited by the stop 25, the distance is always designated by L, which designates the displacement distance of the stop 25, and accordingly the measurement can be effected without being influenced by the possible mechanical resistance of the piston and the cylinder or the like, thus resulting in a precise measurement, without error.

It is also possible to move the stop 25 downwards from the position a after the first pressure P1 is measured, to futher compress the air bubbles in the liquid. In this case, the second pressure P2 is larger than P1.

Finally, according to the apparatus claimed in claim 2, two different volumes of liquid can be easily obtained only by changing the setting of the stop, and the displacement distance of the cylinder piston can be preset at a predetermined value. Therefore this apparatus can be most advantageously adapted to effect the method of the invention.

What is claimed is:

1. An apparatus for measuring the amount of air bubbles contained in an incompressible liquid, said apparatus comprising:
   (a) a first chamber means having valves at each end thereof for receiving the liquid to be measured;
   (b) cylinder means connected to said first chamber means, said cylinder means including a piston movable therein and a second chamber defined by said piston and the walls of said cylinder means, said second chamber being contiguous with and opening into said first chamber means, wherein the movement of said piston varies the volume of said second chamber;
   (c) adjustable stop means operatively coupled to said piston for limiting the movement of said piston to predetermined set positions; and
   (d) pressure gauge means coupled to said first chamber means for measuring the pressure therein.

2. An apparatus as set forth in claim 1, wherein said piston includes a strut member extending therefrom in the direction of movement thereof and wherein said stop means contacts said strut member to stop the movement of said piston at said predetermined set positions.

* * * * *